United States Patent
Benz

(10) Patent No.: US 7,776,351 B2
(45) Date of Patent: Aug. 17, 2010

(54) MOISTURE CURABLE MATERIALS FOR DELIVERY OF AGENTS, METHODS, AND MEDICAL DEVICES

(75) Inventor: Michael E Benz, Ramsey, MN (US)

(73) Assignee: Medtronic, Inc., Minneapolis, MN (US)

( * ) Notice: Subject to any disclaimer, the term of this patent is extended or adjusted under 35 U.S.C. 154(b) by 1273 days.

(21) Appl. No.: 10/842,227

(22) Filed: May 10, 2004

(65) Prior Publication Data

US 2004/0228902 A1 Nov. 18, 2004

Related U.S. Application Data

(60) Provisional application No. 60/470,053, filed on May 13, 2003.

(51) Int. Cl.
- A61F 13/00 (2006.01)
- A01N 55/00 (2006.01)
- A61K 31/695 (2006.01)
- C07F 7/00 (2006.01)
- C07F 7/04 (2006.01)
- C07F 7/08 (2006.01)

(52) U.S. Cl. .......... 424/423; 424/422; 514/63; 556/406; 556/443; 556/464

(58) Field of Classification Search .......... None
See application file for complete search history.

(56) References Cited

U.S. PATENT DOCUMENTS

| | | | |
|---|---|---|---|
| 3,595,885 A * | 7/1971 | Rossmy et al. ............. 554/77 |
| 3,857,825 A | 12/1974 | Streck et al. | |
| 3,920,714 A | 11/1975 | Streck | |
| 3,920,715 A | 11/1975 | Streck et al. | |
| 3,929,850 A | 12/1975 | Streck et al. | |
| 4,891,225 A | 1/1990 | Langer et al. | |
| 5,135,516 A * | 8/1992 | Sahatjian et al. ............. 604/265 |
| 5,142,010 A * | 8/1992 | Olstein ............. 526/248 |
| 5,474,767 A * | 12/1995 | Tremont ............. 424/78.27 |
| 5,521,255 A | 5/1996 | Roy | |
| 5,525,357 A | 6/1996 | Keefer et al. | |
| 5,561,210 A | 10/1996 | Roy | |
| 5,607,691 A | 3/1997 | Hale et al. | |
| 5,676,963 A | 10/1997 | Keefer et al. | |
| 5,714,257 A | 2/1998 | Shah et al. | |
| 5,744,180 A * | 4/1998 | Cherukuri et al. ............. 426/99 |
| 5,756,145 A * | 5/1998 | Darouiche ............. 427/2.24 |
| 5,786,412 A | 7/1998 | Shah et al. | |
| 5,808,126 A | 9/1998 | Brzezinska et al. | |
| 5,837,228 A | 11/1998 | Shih et al. | |
| 5,879,697 A * | 3/1999 | Ding et al. ............. 424/422 |
| 5,900,245 A | 5/1999 | Sawhney et al. | |
| 6,077,916 A | 6/2000 | Laurencin et al. | |
| 6,083,524 A | 7/2000 | Sawhney et al. | |
| 6,143,309 A * | 11/2000 | Legrow et al. ............. 424/401 |
| 6,172,250 B1 * | 1/2001 | Seguin et al. ............. 556/407 |
| 6,252,032 B1 | 6/2001 | Van Antwerp et al. | |
| 6,307,081 B1 | 10/2001 | Takiuchi et al. | |
| 6,468,519 B1 | 10/2002 | Uhrich | |
| 6,486,214 B1 | 11/2002 | Uhrich | |
| 6,787,179 B2 * | 9/2004 | Timm et al. ............. 427/2.24 |
| 7,291,165 B2 * | 11/2007 | Rosenthal et al. ............. 623/1.15 |
| 2003/0204238 A1 * | 10/2003 | Tedeschi ............. 623/1.11 |

FOREIGN PATENT DOCUMENTS

| | | |
|---|---|---|
| EP | 0 482 554 A2 | 4/1992 |
| EP | 0 712 635 A1 | 5/1996 |
| EP | 0 816 465 A2 | 1/1998 |
| EP | 0 982 041 A1 | 3/2000 |
| EP | 0 992 252 A2 | 4/2000 |
| WO | WO 92/00047 | 1/1992 |
| WO | WO 99/30561 | 6/1999 |
| WO | WO 00/78302 A1 | 12/2000 |
| WO | WO 02/30483 A1 | 4/2002 |
| WO | WO 03/090804 A1 | 11/2003 |
| WO | WO 2004/026935 A1 | 4/2004 |

OTHER PUBLICATIONS

Trujillo et al. www2.csusm.edu/DandB/Ethanol.htm 1996.*
Narain et al. Indian Journal of Chemistry 1978 16A:355-356).*
Lukasiak et al. Roczniki Chemii Annales Societatis Chimicae Polonorum 1974 48:1099-1101.*
Hatefi et al., "Biodegradable injectable in situ forming drug delivery systems," *Journal of Controlled Release*. Apr. 23, 2002; 80(1-3):9-28.
Narain et al., "Reactions of Methyltrimethoxy- & Methyldiethoxy-silanes with Salicylic, Lactic, Mandelic & Benzilic Acids," *Indian. J. Chem.*, Apr. 1978; 16A: 355-356.

* cited by examiner

Primary Examiner—Robert A Wax
Assistant Examiner—Caralynne Helm

(57) ABSTRACT

The present invention provides curable materials, medical devices incorporating such materials, wherein the curable materials are capable of releasing hydrolyzable leaving agents upon hydrolysis that can form agents (e.g., pharmaceutically active agents), and methods of making and using such materials and devices.

18 Claims, No Drawings

MOISTURE CURABLE MATERIALS FOR DELIVERY OF AGENTS, METHODS, AND MEDICAL DEVICES

CROSS-REFERENCE TO RELATED APPLICATIONS

The present application claims the benefit of U.S. Provisional Application No. 60/470,053, filed on May 13, 2003, which is incorporated herein by reference in its entirety.

BACKGROUND

Methods of delivering pharmaceutically active agents are desirable in a variety of applications. For example, to counter the adverse reactions that often accompany a medical implant or insert, pharmaceutically active agents have been applied to or embedded within medical devices. This can be accomplished, for example, by covering the surface with a coating containing the active agent. Accordingly, medical device coatings are known that release a pharmaceutically active agent via dissolution of the active agent or by cleavage of the active agent from the coating.

One approach to the incorporation of a pharmaceutically active agent into a polymeric network is to absorb the active agent into the coating from a solution. Hydrophilic polymers in contact with an aqueous solution of an active agent, such as by soaking the polymer in a solution of the active agent, will swell to contain the solution and absorb the active agent dissolved therein. Upon drying, the polymeric network includes the associated active agent. The use of such a polymeric network as a coating for a medical device allows for the association and immobilization of a water soluble active agent with and/or within the medical device. The active agent can then be released from the coating upon contact with aqueous body fluids.

Such polymeric networks can be biodegradable. For example, biodegradable hydrogels can be carriers for biologically active agents such as hormones, enzymes, antibiotics, antineoplastic agents, and cell suspensions. Proper choice of hydrogel macromers can produce membranes with a range of permeability, pore sizes, and degradation rates suitable for a variety of applications in surgery, medical diagnosis, and treatment.

Bioerodable polymers can also be used that include a pharmaceutically active agent as a subunit of the polymer. See, for example, U.S. Pat. Nos. 5,837,228 and 6,486,214.

Another approach to the association of a pharmaceutically active agent with a polymeric coating is by chemical attachment, e.g., covalent attachment, of the active agent to the coating. For example, coating compositions are known that include a nitric oxide-releasing functional group bound to a polymer. U.S. Pat. Nos. 5,676,963 and 5,525,357 disclose such polymeric coating compositions.

The discussion of prior publications and other prior knowledge does not constitute an admission that such material was published, known, or part of the common general knowledge. Although numerous such materials and methods of delivery of agents, particularly pharmaceutically active agents, are known, other methods and materials are still needed.

SUMMARY OF THE INVENTION

The present invention provides curable materials (preferably biocompatible materials) that are capable of releasing hydrolyzable leaving groups upon hydrolysis. The curable materials can include monomers, oligomers, polymers, or mixtures thereof. Such monomers, oligomers, and polymers are referred to herein as prepolymers (i.e., a material capable of forming a polymer or further polymerizing and/or crosslinking). The prepolymer includes at least one hydrolyzable group bonded to at least one silicon atom.

Significantly, upon contact with an aqueous bodily fluid the prepolymer is hydrolyzed thereby releasing a leaving group, which is preferably a biocompatible material and more preferably a biologically active agent, and a silanol-containing reactive intermediate, which is subsequently cured (i.e., polymerized and/or crosslinked) upon condensation. Thus, the prepolymer is capable of releasing a biologically active agent and curing in situ (i.e., in the body of a subject).

Preferably, the hydrolyzable leaving group forms a biocompatible compound (i.e., the hydrolyzed leaving group) upon hydrolysis of the prepolymer and release of the hydrolyzed group. Alternatively and more preferably, the hydrolyzable leaving group forms a pharmaceutically active agent (i.e., the hydrolyzed leaving group) upon hydrolysis of the prepolymer and release of the hydrolyzed group.

Upon release of the hydrolyzable leaving group, the prepolymer forms a curable intermediate (i.e., a polymerizable and/or crosslinkable intermediate). The curable intermediate is preferably biocompatible and forms a biocompatible polymer upon condensation, preferably in the body of a subject.

Preferably, hydrolyzed leaving group is a pharmaceutically active agent. It preferably includes one or more hydroxyl groups (e.g., an alcohol or phenol), carboxylic acid groups, amine groups (e.g., a primary or secondary amine), urea groups, carbamate groups, amide groups, urethane groups, hemiacetal groups, hemiketal groups, or combinations thereof (e.g., amino acids, vicinal diols, hydroxy acids). Specific examples of pharmaceutically active agents include those selected from the group consisting of salicylic acid, fenbufen, cortisone, ibuprofen, diflunisal, sulindac, difluprednate, prednisone, medrysone, acematacin, indomethacin, meloxicam, camptothecin, benoxinate, benzocaine, procaine, ciprofloxacin, norfloxacin, clofoctol, and combinations thereof.

In one embodiment, the present invention provides an implantable medical device that includes a curable material that includes one or more prepolymers, which can be in the form of monomers, oligomers, polymers, or mixtures thereof. The prepolymer includes at least one silicon atom (per molecule) and at least one hydrolyzable leaving group bonded to at least one silicon atom (per molecule).

In another embodiment, the present invention provides a curable (preferably biocompatible) material that includes one or more prepolymers that include at least one silicon atom and at least one hydrolyzable leaving group bonded to at least one silicon atom, wherein the hydrolyzable leaving group forms a pharmaceutically active agent upon hydrolysis of the prepolymer and release of the hydrolyzable leaving group.

The prepolymer can include a wide variety of ratios of silicon atoms to hydrolyzable groups. For example, the prepolymer can include one or more silicon atoms per one hydrolyzable group, wherein the hydrolyzable group can be a terminal group bonded to the silicon atom. Alternatively, the prepolymer can include one silicon atom per one or two hydrolyzable groups or per one to three hydrolyzable groups. Alternatively, the prepolymer can include two silicon atoms per one hydrolyzable group, wherein the hydrolyzable group can be bonded to the two silicon atoms to form a linear polymer or a ring. Alternatively, the prepolymer can include one or more silicon-bonded hydrolyzable leaving groups pendant from a polymeric chain.

In certain embodiments, the prepolymer is a polymer and further includes a poly(alkylene oxide) segment, a polysiloxane segment, a polyester segment, a poly(vinyl pyrrolidone) segment, a polyacrylate segment, a polymethacrylate segment, a polycarbonate segment, a hydrocarbon segment, a polycarbosilane segment, a fluoropolymeric segment, a polyoxazoline segment, or mixtures or copolymers thereof.

In certain embodiments, the hydrolyzable leaving group forms a biocompatible compound upon hydrolysis of the prepolymer and release of the hydrolyzable leaving group. In other embodiments, the hydrolyzable leaving group forms a pharmaceutically active agent upon hydrolysis of the prepolymer and release of the hydrolyzable leaving group.

In certain embodiments, a curable intermediate is formed upon hydrolysis of the prepolymer and release of the hydrolyzable leaving group. This curable intermediate typically and preferably forms a biocompatible polymer upon condensation in the body of a subject. Preferably, the curable intermediate includes at least two silanol groups.

The prepolymer can be formed by polymerizing a polymerizable monomer that includes at least one silicon atom and at least one hydrolyzable leaving group bonded to at least one silicon atom. The polymerizable monomer can be formed by reacting a pharmaceutically active agent and a silicon-containing starting material of the formula $SiX_xR_y$, wherein: each X is independently a halogen, pseudohalogen, alkoxy, or acetoxy; each R is independently hydrogen or an organic group; and $x=0-4$, $y=0-4$, and $x+y=4$. The polymerizing reaction can be, for example, a hydrosilylation reaction or an alkene metathesis reaction.

Alternatively, the polymerizable monomer can be formed by reacting a pharmaceutically active agent and a silicon starting material of the formula $X_{x'}R_{y'}Si-R^1-SiX_{x'}R_{y'}$, wherein: each X is independently a halogen or pseudohalogen; each R is independently hydrogen or an organic group; $R^1$ is an alkylene, a divalent siloxane, a divalent oligo- or poly-alkylene oxide, a divalent carbosilane; and $x'=0-3$, $y'=0-3$, and $x'+y'=3$. Alternatively, this same silicon starting material can be used to make the prepolymer per se.

Alternatively, the prepolymer can be formed directly by reacting a pharmaceutically active agent and a silicon-containing polymer.

As used herein, a "biocompatible" material or compound may be defined as a material or compound that is substantially insoluble in body fluids and tissues and that is designed and constructed to be placed in or onto the body or to contact fluid or tissue of the body. Ideally, a biocompatible material or compound will not induce undesirable reactions in the body such as blood clotting, tissue death, tumor formation, allergic reaction, foreign body reaction (rejection) or inflammatory reaction; will have the physical properties such as strength, elasticity, permeability and flexibility required to function for the intended purpose; can be purified, fabricated and sterilized easily; and will substantially maintain its physical properties and function during the time that it remains implanted in or in contact with the body.

As used herein, a "medical device" may be defined as a device that has surfaces that contact tissue, bone, blood or other bodily fluids in the course of their operation, which fluids are subsequently used in patients. This can include, for example, extracorporeal devices for use in surgery such as blood oxygenators, blood pumps, blood sensors, tubing used to carry blood and the like which contact blood which is then returned to the patient. This can also include endoprostheses implanted in blood contact in a human or animal body such as vascular grafts, stents, pacemaker leads, heart valves, and the like, that are implanted in blood vessels or in the heart. This can also include devices for temporary intravascular use such as catheters, guide wires, and the like which are placed into the blood vessels or the heart for purposes of monitoring or repair. Preferably, medical devices of the present invention are implantable medical devices (i.e., those that are implanted into a body and remain in the body for an extended period (e.g., greater than 28 days)).

As used herein, the terms "pharmaceutically active agent," "biologically active agent," and "active agent," are used interchangeably and include pharmacologically active substances that produce a local or systemic effect in an animal. The terms thus mean any substance intended for use in the diagnosis, cure, mitigation, treatment, or prevention of disease or in the enhancement of desirable physical or mental development and conditions in a subject.

The term "subject" used herein is taken to include humans, sheep, horses, cattle, pigs, dogs, cats, rats, mice, birds, reptiles, fish, insects, arachnids, protists (e.g., protozoa), and prokaryotic bacteria. Preferably, the subject is a human or other mammal.

The terms "comprises" and variations thereof do not have a limiting meaning where these terms appear in the description and claims.

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

The present invention provides curable materials (preferably biocompatible materials) that are capable of releasing hydrolyzable leaving groups (preferably, biologically active agents) upon hydrolysis. The curable material includes one or more prepolymers that include at least one hydrolyzable group bonded to silicon. The prepolymers may include polymers, monomers, oligomers, or mixtures thereof. The curable materials are referred to herein as "curable" because they form intermediates that are curable (which can occur through polymerization, crosslinking, or both). These intermediates are the molecules remaining after hydrolysis of the prepolymer and release of the hydrolyzable leaving group. The curable intermediate is also preferably biocompatible. Upon condensation of the intermediate, a biocompatible polymer is formed, preferably in the body of a subject. Preferably, the curable intermediate includes at least two silanol groups, which are capable of undergoing condensation.

Significantly, in preferred embodiments, upon contact with an aqueous bodily fluid the curable material is hydrolyzed, thereby cleaving the bond or bonds between the hydrolyzable group(s) and silicon atom(s) and forming biologically active agent(s) and silanol-containing reactive intermediate(s), which can subsequently cure (i.e., polymerize and/or crosslink) upon condensation. Thus, a preferred curable material of the present invention is capable of releasing a biologically active agent and polymerizing in situ.

It has been discovered that incorporation of a biologically active agent into a polymeric matrix provides a polymer-bound active agent adduct composition that can be applied with specificity to a biological site of interest. Site specific application of the polymer-bound adduct composition enhances the selectivity of action of the active agent. If active agents attached to the polymer are necessarily localized, then the effect of the release of the active agents will be concentrated in the tissues with which they are in contact.

The curable materials of the present invention are capable of releasing such biologically active agents, or other hydrolyzable leaving groups, ispontaneously upon contacting an aqueous environment. That is, they do not require activation through a redox reaction or electron transfer reaction such as is required for glyceryl trinitrate and sodium nitroprusside. Preferably, the active agents, or other hydrolyzable leaving groups, are released under physiological conditions.

Although it is preferred that the hydrolyzable leaving group forms a biocompatible compound (i.e., the hydrolyzed leaving group) upon hydrolysis of the prepolymer and release of the hydrolyzed group, it is not a requirement that such released compound be biocompatible.

In some embodiments, it may be advantageous to release molecules other than pharmaceutically active molecules. In these embodiments, a prepolymer may be designed such that the molecule released has minimal physiological effect, as an alternative to pharmaceutically active molecules. Such molecules include amino acids, alditols, synthetic polyols (such as pentaerythritol), carbohydrates, alcohols, fatty acids, vitamins, aspartame, glyceraldehydes, and the like. For example, the dosage of a pharmaceutically active agent could be controlled by synthesizing the prepolymer from starting materials that are derived from both the desired active agent and from other molecules that can undergo hydrolysis, but have minimal physiological effect. In other embodiments, it may be desirable to release only a small molecule (preferably less than 1000 grams per mole (g/mol), and more preferably less than 200 g/mol) from the prepolymer that is not pharmaceutically active. For example, if it is desirable that the prepolymer show low shrinkage as it cures, use of such a small molecule may facilitate this goal.

Alternatively and more preferably, the hydrolyzable leaving group forms a pharmaceutically active agent (i.e., the hydrolyzed leaving group) upon hydrolysis of the prepolymer and release of the hydrolyzed group.

The active agents that can be delivered according to the present invention include inorganic and organic drugs, without limitation, and include drugs that act on the peripheral nerves, adrenergic receptors, cholinergic receptors, nervous system, skeletal muscles, cardiovascular system, smooth muscles, blood circulatory system, synaptic sites, neuro-effector junctional sites, endocrine system, hormone systems, immunological system, reproductive system, skeletal system, autocoid systems, alimentary and excretory systems (including urological systems), histamine systems, and the like. Such conditions, as well as others, can be advantageously treated using the materials of the present invention.

For example, currently used injectable agents in the treatment of female stress urinary incontinence include polytetrafluoroethylene, autologous fat, collagen, silicone microparticles, silicone microballoons, and pyrolytic carbon. All of these materials have drawbacks, such as particle migration or decreased efficacy over time. None of them is more than about 70% effective over long time periods. There exists a need for better injectable materials that are not particulate (to prevent migration) and that maintain their physical properties and effectiveness for longer periods. Polymers have also been injected near the lower esophageal sphincter to mitigate gastroesophageal reflux disease. Current approaches include injecting a solid prosthesis fabricated from a dehydrated hydrophilic polymer and injecting poly(vinyl alcohol) which has been dissolved in dimethylsulfoxide. In both of these applications, releasing a pharmaceutically active agent as the injected polymer cures may improve patient outcomes or recovery.

The active agents that can be delivered using the materials of the present invention include, but are not limited to, anticonvulsants, analgesics, antiparkinsons, antiinflammatories (e.g., ibuprofen, fenbufen, cortisone, and the like), calcium antagonists, anesthetics (e.g., benoxinate, benzocaine, procaine, and the like), antibiotics (e.g., ciprofloxacin, norfloxacin, clofoctol, and the like), antimalarials, antiparasitics, antihypertensives, antihistamines, antipyretics, alpha-adrenergic agonists, alpha-blockers, biocides, bactericides, bronchial dilators, beta-adrenergic blocking drugs, contraceptives, cardiovascular drugs, calcium channel inhibitors, depressants, diagnostics, diuretics, electrolytes, enzymes, hypnotics, hormones, hypoglycemics, hyperglycemics, muscle contractants, muscle relaxants, neoplastics, glycoproteins, nucleoproteins, lipoproteins, ophthalmics, psychic energizers, sedatives, steroids sympathomimetics, parasympathomimetics, tranquilizers, urinary tract drugs, vaccines, vaginal drugs, vitamins, collagen, hyaluronic acid, nonsteroidal anti-inflammatory drugs, angiotensin converting enzymes, polynucleotides, polypeptides, polysaccharides, and the like.

Preferably, a pharmaceutically active agent (or other hydrolyzed, i.e., released, leaving group) includes one or more active hydrogen atoms. These can be present in one or more hydroxyl groups (e.g., an alcohol or phenol), carboxylic acid groups, amine groups (e.g., a primary or secondary amine), urea groups, carbamate groups, amide groups, urethane groups, hemiacetal groups, hemiketal groups, or combinations thereof (e.g., amino acids, vicinal diols, hydroxy acids).

Exemplary active agents include, but are not limited to, salicylic acid, fenbufen, cortisone, ibuprofen, diflunisal, sulindac, difluprednate, prednisone, medrysone, acematacin, indomethacin, meloxicam, camptothecin, benoxinate, benzocaine, procaine, ciprofloxacin, norfloxacin, clofoctol, and combinations thereof. Preferred active agents are salicylic acid, fenbufen, cortisone, ibuprofen, diflunisal, and sulindac, which are shown below. Any one prepolymer can include two or more different active agents.

Salicylic acid

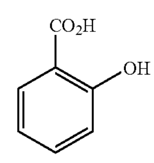

Cortisone

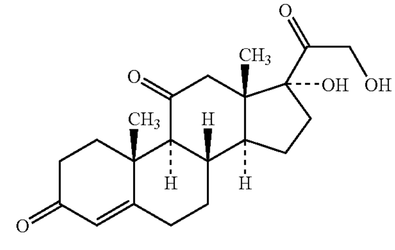

-continued

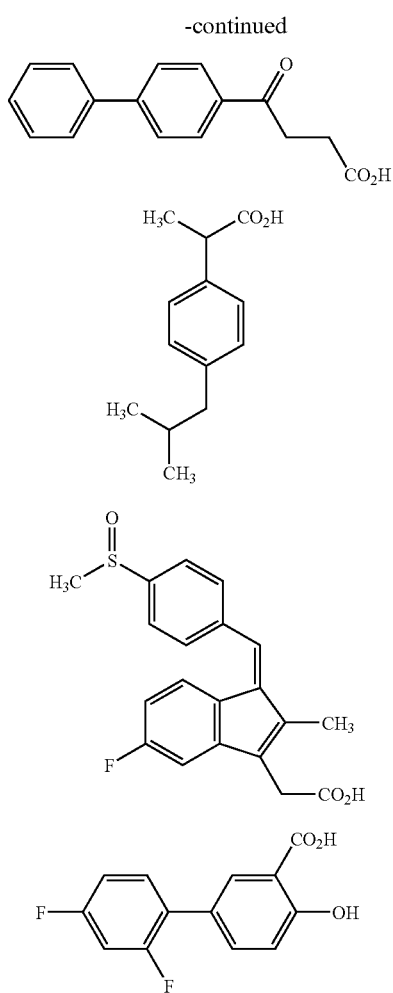

Fenbufen

Ibruprofen

Sulinac

Diflunisal

In addition to silicon and at least one hydrolyzable group bonded to silicon, certain exemplary curable materials are polymeric (although they may also be oligomeric and monomeric). If the prepolymers are polymeric, they preferably further include a polymeric segment such as a poly(alkylene oxide) segment, a polysiloxane segment, a polyester segment, a poly(vinyl pyrrolidone) segment, a polyacrylate segment, a polymethacrylate segment, a polycarbonate segment, a hydrocarbon segment, a polycarbosilane segment, a fluoropolymeric segment, a polyoxazoline segment, or mixtures or copolymers thereof. Such segments typically form a polymer backbone. Preferred such polymer backbones include a polysiloxane segment, a poly(alkylene oxide) segment, a hydrocarbon segment, a polycarbosilane segment, or mixtures or copolymers thereof. Combination of different polymeric segments can be included in any one prepolymer.

The following structures are representations of compounds wherein the arcs or wavy lines represent a polymer backbone (i.e., the polymer segments listed above), M represents the hydrolyzable leaving group (e.g., a group derived from the desired active agent to be delivered), and R represents non-reactive organic groups, such as methyl. Preferred R groups include up to 20 carbon atoms and may optionally include oxygen atoms in the chain as in oligo(alkylene oxides).

In certain embodiments, the curable material includes a prepolymer that includes one or more silicon atoms per one hydrolyzable group. Such hydrolyzable group can be a terminal group bonded to the silicon atom, although this is not a requirement. Examples of such a material are represented by the following four structures:

I

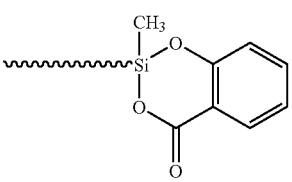

II

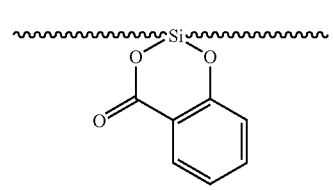

III

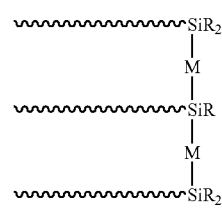

IV

In structure I, the prepolymer is linear and would yield a linear polymer upon hydrolysis and condensation.

In structure II, the prepolymer is shown with the pharmaceutically active agent salicylic acid as M. Upon hydrolysis and condensation, this prepolymer would generate a comb or brush polymer. For example, the backbone of the comb polymer would be a polysiloxane, and the teeth of the comb polymer would be formed by the polymer tail shown as the wavy line, which could be poly(ethylene oxide), for example.

In structure III, the prepolymer would generate a denser comb upon hydrolysis and condensation due to the presence of two tails per silicon atom.

In structure IV, the prepolymer would form a comb polymer that has a polysiloxane backbone. The teeth of the comb would correspond to the polymeric segment represented by the wavy line.

In certain embodiments, the curable material includes a prepolymer that includes one silicon atom per one or two hydrolyzable groups. Examples of such a material is represented by the following two structures:

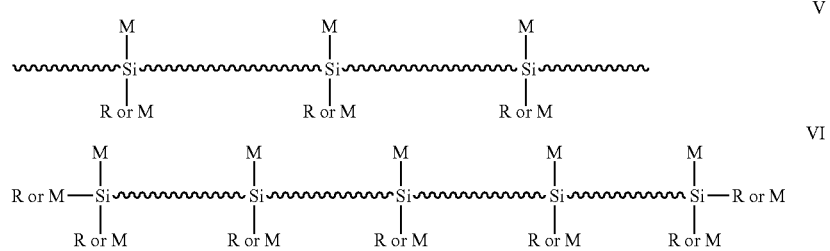

V

VI

In structure V, the prepolymer would yield a crosslinked polymer with free chain ends upon hydrolysis and condensation.

In structure VI, the prepolymer would yield a crosslinked polymer with no free chain ends upon hydrolysis and condensation.

In certain embodiments, the curable material includes a prepolymer that includes one silicon atom per one to three hydrolyzable groups. Examples of such a material is represented by the following two structures:

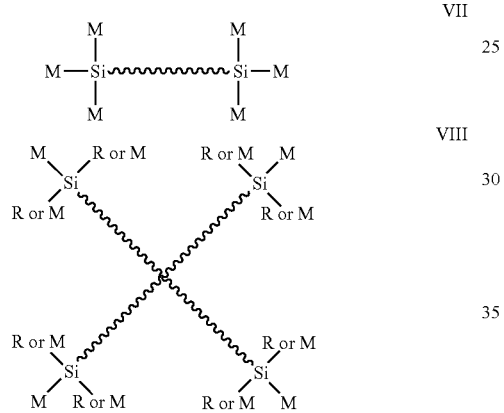

VII

VIII

In structure VII, the prepolymer would yield a crosslinked polymer upon hydrolysis and condensation. The M's could be separate moieties or they could represent a multi-functional (e.g., di- or tri-functional) hydrolyzable leaving group.

In structure VIII, the prepolymer is star-shaped. The M's could be separate moieties or they could represent a multi-functional (e.g., di- or tri-functional) hydrolyzable leaving group.

In certain embodiments, the curable material includes a prepolymer that includes one hydrolyzable group bonded to two silicon atoms. Examples of such a material are represented by the following two structures:

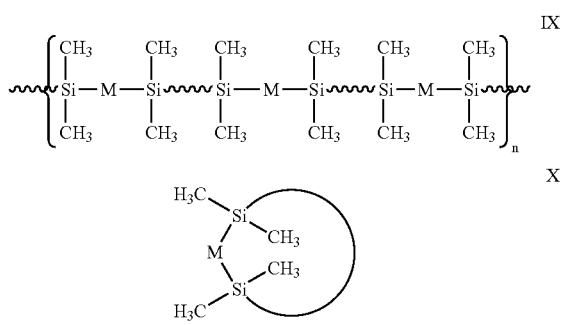

IX

X

In structure IX, the hydrolyzable group is bonded to the two silicon atoms to form a linear polymer. The prepolymer would yield a linear polymer upon hydrolysis and condensation with the M's being replaced by oxygen atoms.

In structure X, the hydrolyzable group is bonded to two silicon atoms to form a ring. The prepolymer would yield a linear polymer upon hydrolysis and condensation with the backbone segments joined by tetramethyldisiloxane moieties.

In certain embodiments, the curable material includes a prepolymer that includes one or more silicon-bonded hydrolyzable groups pendant from the main chain of a polymer. An example of such a material is represented by the structure shown in the following reaction scheme:

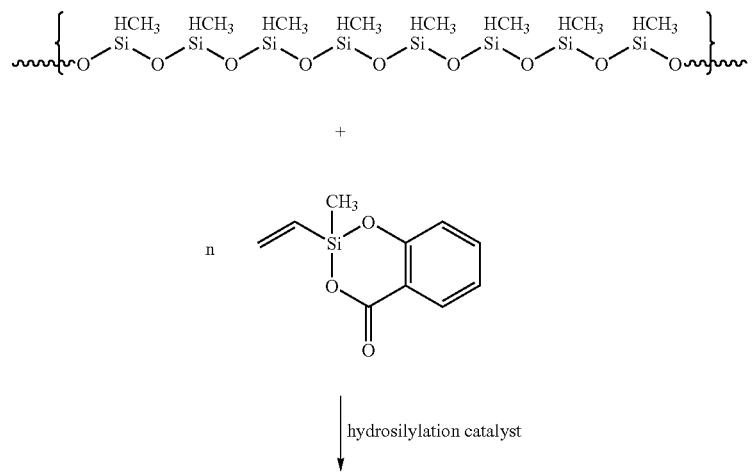

-continued

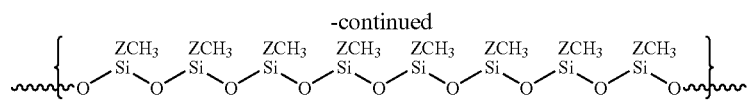

Where Z represents the moiety 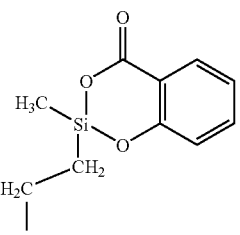

Prepolymers of the present invention can be made in a number of ways. For example, in certain embodiments, the prepolymer can be formed by polymerizing a polymerizable monomer comprising silicon and a hydrolyzable leaving group. The polymerizable monomers include at least one polymerizable group attached to the silicon. Examples of polymerizable groups include ethylenically unsaturated groups (e.g., —CH=CH$_2$, (meth)acrylates, —CH$_2$CH$_2$CH$_2$CH=CH$_2$) and active hydrogen atoms.

Examples of polymerizable monomers include those shown below with a salicylic acid (Compounds 1-5), fenbufen (Compound 6), or benzocaine (Compounds 7 and 8) precursors as the hydrolyzable leaving group:

Compound 1
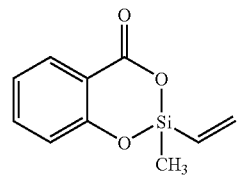

Compound 2
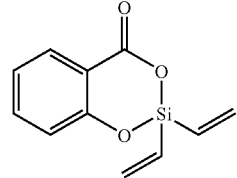

Compound 3
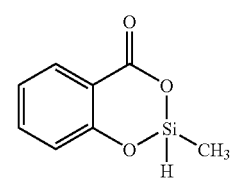

Compound 4
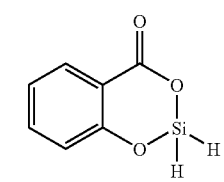

-continued

Compound 5
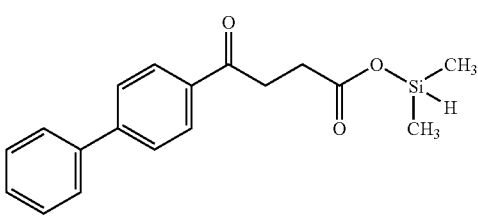

Compound 6
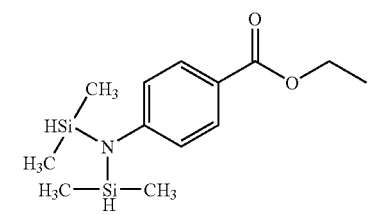

Compound 7
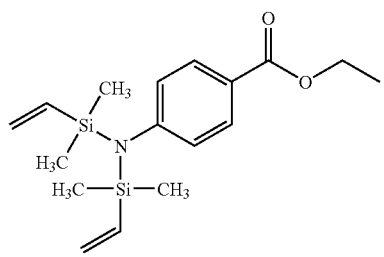

Compound 8

Polymerizable monomers can be formed by reacting a pharmaceutically active agent and a silicon-containing starting material. Typically, at least one silicon-containing starting material is reacted with at least one pharmaceutically active agent (preferably with at least one active hydrogen atom) to form the polymerizable monomer.

A preferred silicon-containing starting material is of the formula SiX$_x$R$_y$, wherein: each X is independently a halogen (preferably, chlorine), pseudohalogen (preferably, nitrile), alkoxy (preferably, a C1-C20 alkoxy, and more preferably, methoxy or ethoxy), or acetoxy (preferably, C1-C20 acetoxy, and more preferably, acetyloxy)); each R is independently hydrogen or an organic group; and x=0-4, y=0-4, and x+y=4. Preferably, each R is independently hydrogen, an alkyl (preferably, C1-C20 alkyl, and more preferably, C1-C10 alkyl), an alkenyl (preferably, C3-C20 alkenyl in which at least one double bond is within six carbons from the terminus, and more preferably, vinyl), a vinyl ether (e.g., —CH$_2$CH$_2$—O—CH=CH$_2$), an allyl (e.g., —CH$_2$CH=CH$_2$), an allyl ether (e.g., —CH$_2$CH$_2$OCH$_2$CH=CH$_2$), an alkynyl (e.g., ethynyl, —C≡—CH), a (meth)acrylate (e.g., CH$_2$=C(CH$_3$)CO$_2$CH$_2$CH$_2$—), or an acrylamide (e.g., CH$_2$=CHCON(CH$_3$)CH$_2$CH$_2$—). Examples of silicon-containing starting materials include SiCl$_2$(CH$_3$)(CH=CH$_2$), SiCl$_2$(CH=CH$_2$)$_2$, SiCl$_2$H$_2$, SiCl$_2$H(CH$_3$), SiCl(CH$_3$)$_2$(CH=CH$_2$), SiClH(CH$_3$)$_2$, SiCl$_4$, SiCl$_3$(CH$_3$), and SiCl(CH$_3$)(CH=CH$_2$)$_2$.

The polymerizable monomers can be reacted with other polymerizable monomers to form prepolymers of the present invention. A wide variety of monomers that do not include silicon can be used. Examples include vinyltelechelic poly(ethylene glycol) or poly(propylene glycol), 1,5-hexadiene, and 1,7-octadiene. They can also be reacted with monomers that do contain silicon atoms, such as dimethyldivinylsilane, trimethylsilane, trimethylvinylsilane, and the following compound (Compound 9 in the Examples Section):

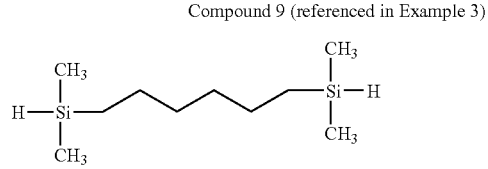

Compound 9 (referenced in Example 3)

The polymerization reaction can involve a variety of mechanisms including hydrosilylation, alkene metathesis, vinyl radical polymerization, ring opening polymerization, ionic polymerization (including anionic polymerization).

Exemplary reaction schemes for forming prepolymers by initially reacting a silicon-containing starting material with a pharmaceutically active agent are shown below:

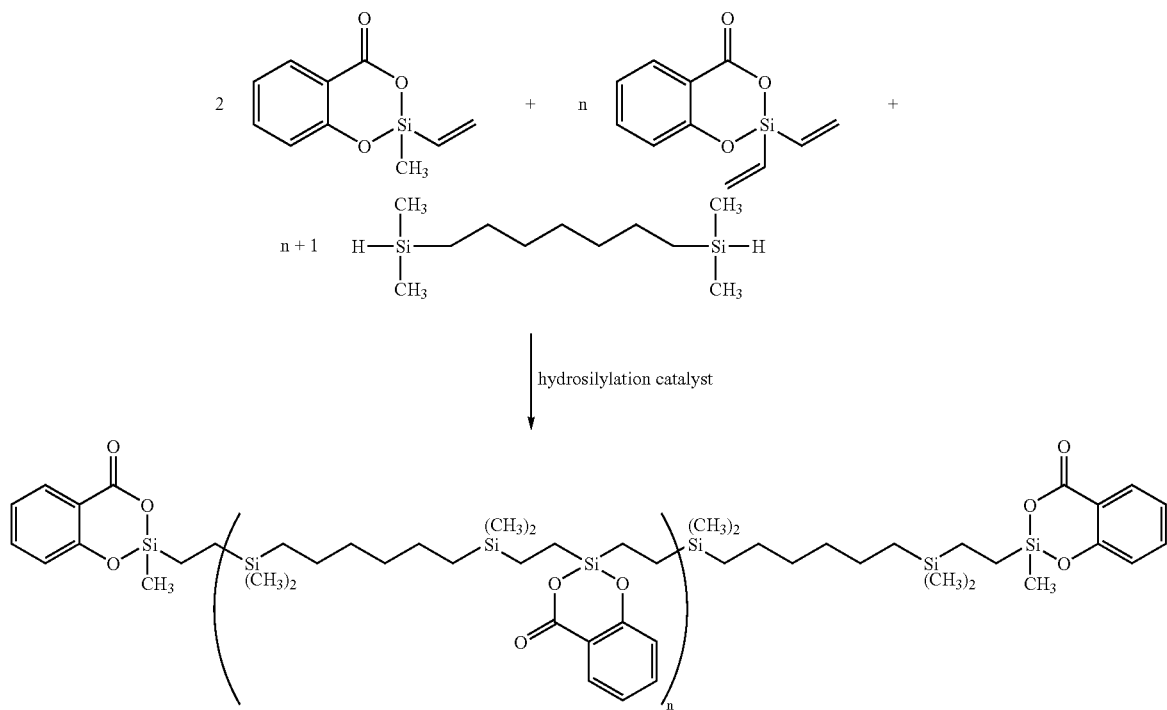

Alternatively, the same reactive prepolymer may be synthesized by the route shown below:

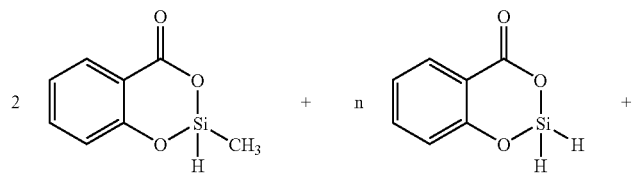

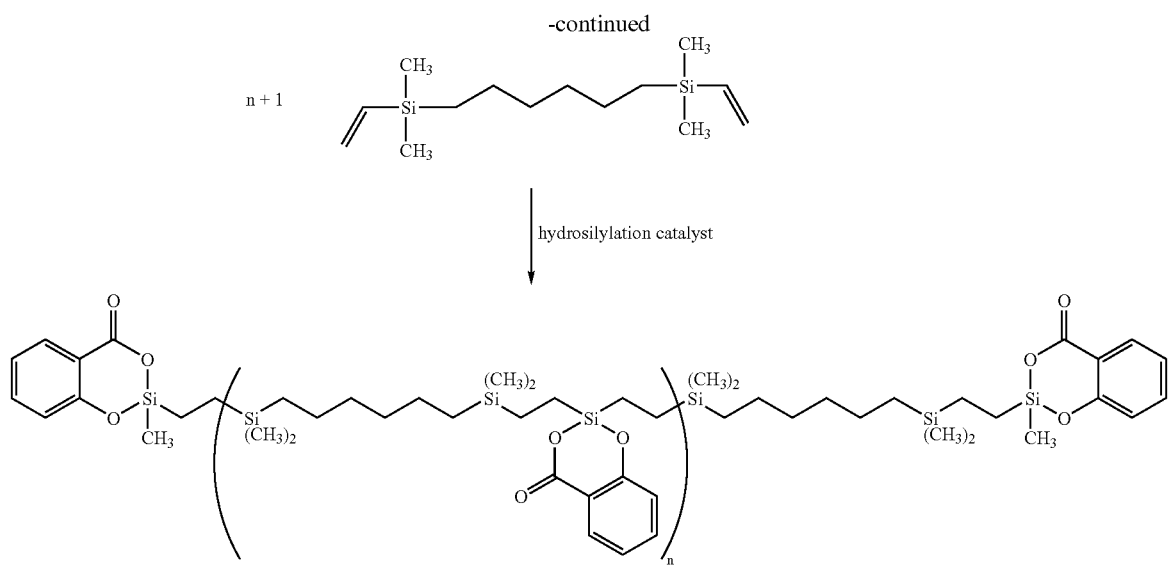

Prepolymers of the present invention can also be prepared directly by reacting a pharmaceutically active agent and a silicon-containing starting material. For example, a silicon starting material of the formula $X_{x'}R_{y'}Si—R^1—SiX_{x'}R_{y'}$ can be used wherein: each X is independently a halogen (preferably, chlorine), pseudohalogen (preferably, nitrile), alkoxy (preferably, a C1-C20 alkoxy, and more preferably, methoxy or ethoxy), or acetoxy (preferably, C1-C20 acetoxy, and more preferably, acetyloxy; $R^1$ is an alkylene, a siloxane, an oligo- or poly(alkylene oxide), a carbosilane; each R is independently hydrogen or an organic group; and x'=0-3, y'=0-3, and x'+y'=3. Preferably, each R is independently hydrogen, an alkyl (preferably, C1-C20 alkyl, and more preferably, C1-C10 alkyl), an alkenyl (preferably, C3-C20 alkenyl in which at least one double bond is within six carbons from the terminus, and more preferably, vinyl), a vinyl ether (e.g., —CH$_2$CH$_2$—O—CH═CH$_2$), an allyl (e.g., —CH$_2$CH═CH$_2$), an allyl ether (e.g., —CH$_2$CH$_2$OCH$_2$CH═CH$_2$), an alkynyl (e.g., ethynyl, —C≡CH), a (meth)acrylate (e.g., CH$_2$═C(CH$_3$)CO$_2$CH$_2$CH$_2$—), or an acrylamide (e.g., CH$_2$═CHCON(CH$_3$)CH$_2$CH$_2$—). Examples of silicon starting materials include the following:

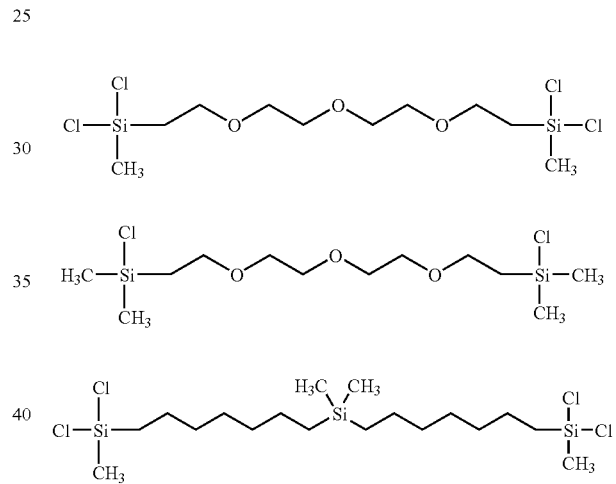

Exemplary reaction schemes for forming prepolymers by directly reacting a silicon-containing starting material with a pharmaceutically active agent are shown below:

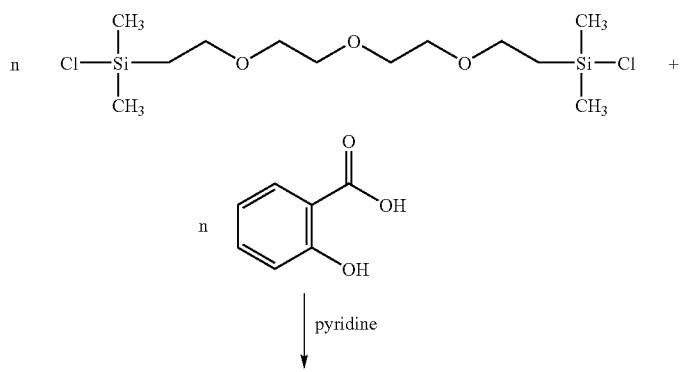

-continued

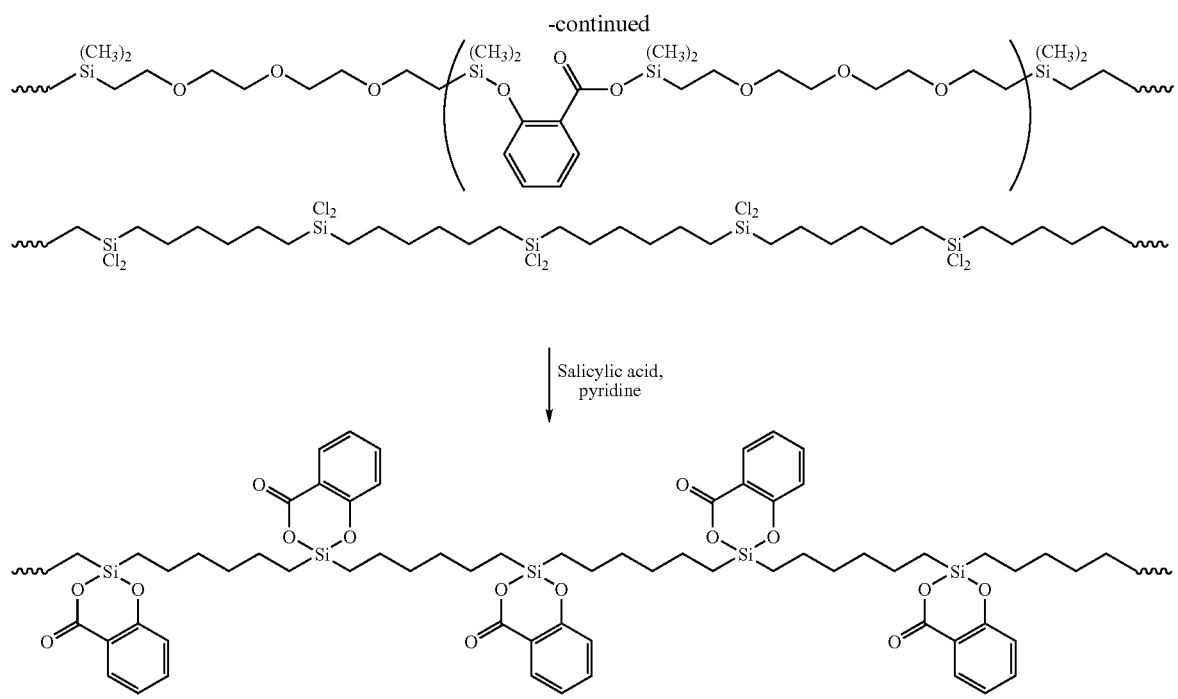

Prepolymers of the present invention can be used in various combinations for various applications. They can be used as tissue-bulking agents in urological applications for bulking the urinary sphincter to prevent stress incontinence or in gastrological applications for bulking of the lower esophageal sphincter to prevent gastroesophageal reflux disease. They can be used for replacements for nucleus pulposis or repair of annulus in intervertebral disc repair procedures. They can be used as tissue adhesives or sealants. They can be used as surgical void fillers, for example, in reconstructive or cosmetic surgery (e.g., for filling a void after tumor removal). They can be used to repair aneurysms, hemorrhagic stroke or other conditions precipitated by failure of a blood vessel. They can be used as an antiadhesion agent. They can be used in a wide variety of other applications in which a material is needed that will increase strength and/or modulus after implantation.

Prepolymers of the present invention can be used in injectable compositions. Such injectable materials could be used as tissue bulking agents (e.g., for the treatment of urinary stress incontinence, for the treatment of gastroesophageal reflux disease, or serving to augment a degenerated intervertebral disc), void fillers (e.g., in cosmetic or reconstructive surgery, such as serving as a replacement for the nucleus pulposis), or as an injectable drug delivery matrix.

In some embodiments, no additives would be needed to form an injectable composition. In some embodiments, one or more prepolymers can be combined with a solvent such as dimethylsulfoxide (DMSO), which is a fairly biocompatible solvent. The DMSO diffuses away after injection and the polymer remains in place.

Also, injectable compositions could include crosslinkers (such as triethoxymethylsilane), plasticizers (such as dioctyl phthalate), lipids (soybean oil), poly(ethylene glycol) (with the ends blocked with methyls or similar groups), silicone oil, partially or fully fluorinated hydrocarbons, N-methyl-2-pyrrolidone, or mixtures thereof.

Prepolymers of the present invention can be used in combination with a variety of particulate materials. For example, they can be used with moisture curing ceramic materials (e.g., tricalcium phosphate) for vertebroplasty cements, bone void filling (due to disease such as cancer or due to fracture). They can be used in combination with inorganic materials such as hydroxylapatite to form pastes for use in bone healing, sealing, filling, repair, and replacement. They can be used in combination with polymer microspheres that can be reservoirs for a biologically active agent such as a protein, DNA plasmid, RNA plasmid, antisense agent, etc. Alternatively, they can be used in combination with solid polymer particulate materials, such as polytetrafluoroethylene for forming a composite matrix with greater modulus than that provided by the polymer alone, or imaging particulate materials such as barium sulfate for visualizing material placement using fluoroscopy, for example. They can be combined with fibers, woven or nonwoven fabric for reconstructive surgery, such as the in situ formation of a bone plate or a bone prosthesis.

Curable materials of the present invention can also be applied to a desired site (e.g., a surgical site) using a syringe, catheter, or by hand.

Alternatively, curable materials of the present invention can be coated onto a substrate if desired. A coating mixture of the prepolymer can be prepared using solvents such as toluene, chloroform, tetrahydrofuran, perfluorinated solvents, as well as other organic solvents that can be rendered moisture-free and have no active hydrogens. The coating mixture can be applied to an appropriate substrate such as polymer coated medical wires, stents, prostheses, penile inserts, and the like, by conventional coating application methods. Such methods include, but are not limited to, dipping, spraying, wiping, painting, solvent swelling, and the like. After applying the coating solution to a substrate, the solvent is preferably allowed to evaporate from the coated substrate.

The materials of a suitable substrate include, but are not limited to, polymers, metal, glass, ceramics, composites, and multilayer laminates of these materials. The coating may be applied to metal substrates such as the stainless steel used for guide wires, stents, catheters and other devices. Organic substrates that may be coated with the prepolymers of this invention include, but are not limited to, polyether-polyamide block copolymers, polyethylene terephthalate, polyetherurethane, polyesterurethane, other polyurethanes, natural rubber, rubber latex, synthetic rubbers, polyester-polyether copolymers, polycarbonates, and other organic materials.

Additives that can be combined with the curable material in a composition include, but are not limited to, wetting agents for improving wettability to hydrophobic surfaces, viscosity and flow control agents to adjust the viscosity and thixotropy of the mixture to a desired level, antioxidants to improve oxidative stability of the cured coatings, dyes or pigments to impart color or radiopacity, and air release agents or defoamers, cure catalysts, cure accelerants, plasticizers, solvents, stabilizers (cure inhibitors, pot-life extenders), and adhesion promoters.

Objects and advantages of this invention are further illustrated by the following examples, but the particular materials and amounts thereof recited in these examples, as well as other conditions and details, should not be construed to unduly limit this invention.

EXAMPLES

All reactions were performed in a nitrogen or argon atmosphere using flame- or oven-dried glassware unless otherwise specified. Salicylic acid, anhydrous pyridine, 1,6-dibromohexane, magnesium turnings, chlorodimethylsilane, poly (ethylene glycol) divinyl ether, 2,2'-azobisisobutyronitrile, anhydrous tetrahydrofuran, methyl methacrylate, dichlorodimethylsilane, (S)-(+)4-Isobutyl-α-methylphenylacetic acid, and anhydrous toluene were purchased from the Sigma-Aldrich Corporation, Milwaukee, Wis. Anhydrous stabilizer-free tetrahydrofuran was purchased from Alfa-Aesar, Ward Hill, Mass. Divinyldimethylsilane, 1,8-bis(chlorodimethylsilyl)octane, trimethylsilyl-terminated dimethylsiloxane-methylhydrosiloxane copolymer (3-4 weight percent methylhydrosilane), 3-acryloxypropylmethyldichlorosilane, and platinum-divinyltetramethyldisiloxane (2-3% platinum in xylenes) hydrosilylation cayalyst were purchased from United Chemical Technologies, Inc., Bristol, Pa. The tricyclohexylphosphine[1,3-bis(2,4,6-trimethylphenyl)-4,5-dihydroimidazol-2-ylidene][benzylidene]ruthenium(IV) dichloride metathesis catalyst is available from Strem Chemicals, Inc., Newburyport, Mass. Analysis of sample using nuclear magnetic resonance spectroscopy was performed using a JEOL Eclipse 400 MHz spectrometer (JEOL USA, Inc., Peabody, Mass.).

Example 1

Synthesis of a salicyclic acid-divinylsilane adduct (Compound 2)

In a nitrogen-atmosphere glove box, a dry three-necked round-bottomed 250-mL flask was outfitted with a magnetic stirring bar and two septa. To this flask was added 25 grams divinyldichlorosilane, 22.55 grams salicylic acid, and 150 mL anhydrous toluene. The flask was sealed and transferred to a hood, where it was connected to a condenser outfitted with an adapter connected to a nitrogen line with a bubbler. The flask was outfiftted with a heating mantle connected to a rheostat. The contents of the flask were stirred using a magnetic stirplate and 28 mL anhydrous pyridine were added by syringe. The contents of the flask were brought to reflux and refluxed for one hour, then cooled to room temperature and filtered through a fritted disc under vacuum directly into a single-neck 500 mL flask. The solvent was removed using a rotary evaporator at full oil pump vacuum. The flask was sealed immediately after it was disconnected from the rotary evaporator, and transferred to a nitrogen-atmosphere glovebox. In the glovebox, the contents of the flask were transferred to a 100 mL single-neck round-bottomed flask. This smaller flask was connected to a dried distillation apparatus having a fractionating distilling receiver with four receivers. The product was distilled at about 16 Pa. Two cuts were taken; the first cut distilled at 72-75° C., the second cut distilled 78-83° C. The first cut weighed 6.757 g; the second cut weighed 26.219 g. The two cuts together corresponded to a 93% yield versus theoretical. The structure of the product was confirmed using NMR spectroscopy Example 2

Synthesis of a salicylic acid-methylvinylsilane Adduct (Compound 1)

In the nitrogen glovebox, 97.88 g salicylic acid, 101.0 g dichloromethylvinylsilane and 1296.83 g anhydrous toluene were added to an oven-dried, 3-neck, 3-liter round-bottomed flask. The flask was outfitted with a mechanical stir arm, septum, and a condenser that was closed at the top with a stopper. The flask was taken out of the glovebox and transferred to a hood. The stopper at the top of the condenser was quickly replaced with a nitrogen purge inlet and outlet connected to a bubbler. The mixture of clear liquid and white solid was mechanically stirred. Via cannula and nitrogen pressure, 200 mL anhydrous pyridine was added to the flask. The formation of large white particles and a slight exotherm was noted upon the addition of the pyridine. With a heating mantle and variac, the mixture was brought to reflux and was held there for one hour. Upon heating, the liquid became pale yellow and the precipitate remained white. The heat was turned off and the flask was allowed to cool for 45 minutes.

Nitrogen positive pressure was introduced through the septum, and the condenser was quickly removed and replaced with a septum. The flask was transferred to a nitrogen-atmosphere glovebox to cool completely. The flask was vented during cooling with a needle through one septum. The pyridinium hydrochloride precipitate was removed by water aspirator vacuum filtration. The toluene was then removed by rotary-evaporation. In order to minimize contact with moisture, the rotary-evaporator was purged with nitrogen before the flask was quickly attached. Upon removal of enough solvent, the solution was transferred to an oven-dried, 1 Liter, round-bottomed flask. The solution was placed on the rotary-evaporator at 65° C. and 667 Pa pressure until no more solvent was removed. The product was a clear, brown, slightly viscous liquid.

A distillation apparatus was set up that could be purged with nitrogen to release the vacuum. The product was distilled with a vapor temperature of 125° C. and a pressure of 907 Pa. The temperature measured between the heating mantle and the flask was 217° C. Before the product began distilling, some white crystals collected in the condenser. The precipitate was collected in the first and second cuts, along with the clear and colorless product. The total amount collected in the distillation was 139.26 g, a 94.4% yield. The total amount in the third cut was 60.18 g. This cut was characterized by NMR spectroscopy. The peaks observed by proton NMR were: δ7.98 (d), 7.45 (t), 7.20 (t), 6.92 (d), 6.22 (t), 6.60 (s), 6.40 (s), 0.5 (s). The peaks observed by $^{13}$C NMR were: δ160.5, 156.0, 139.3, 136.1, 132.0, 130.1, 122.3, 120.1, 116.9, −2.84 ppm.

Example 3

Synthesis of 1,6-bis(dimethylsilyl)hexane (Compound 9)

In a nitrogen-atmosphere glovebox, 158.26 g of magnesium turnings were placed in a four-neck twelve-liter round-bottomed flask. The flask was stoppered, then removed to a fume hood where it was equipped with a condenser, two-liter pressure-equalizing addition funnel, a glass thermocouple well, and a glass stirring shaft equipped with a polytetrafluoroethylene blade. The flask was placed in a heating mantle and connected to a source of nitrogen gas through an adapter attached to the condenser. A thermocouple connected to a temperature controller was placed in the well. The stirring shaft was connected to an air motor. Next, 259.4 g 1,6-dibromohexane were transferred to the addition funnel, which was then filled with anhydrous tetrahydrofuran to the two-liter mark. Sixty mL of this solution was then added to the flask. The reaction initiated with a vigorous exotherm. After the exotherm had subsided, 300 mL of anhydrous tetrahydrofuran were added directly to the flask, and the remaining contents of the addition funnel were added dropwise over 100 minutes, at such a rate as to keep the reaction below reflux. The addition funnel was then recharged with 505.19 g 1,6-dibromohexane and anhydrous tetrahydrofuran sufficient to yield two liters of solution. This solution was added over about 160 minutes, again keeping the temperature of the flask below reflux. After all of the 1,6-dibromohexane solution had been added, the reaction was brought to reflux for 90 minutes. Then the heating mantle was turned off and the reaction mixture was stirred under a nitrogen atmosphere for 16 hours. The mantle was removed from under the flask and the addition funnel was recharged with 653.45 g chlorodimethylsilane and anhydrous tetrahydrofuran sufficient to yield about 2100 mL of solution. This solution was added to the flask over 270 minutes, at a rate such that the contents of the flask did not exceed a temperature of about 50° C. After the addition was complete, two additional liters of anhydrous tetrahydrofuran were added to the flask. The heating mantle was returned and the reaction mixture was brought to reflux. After two hours at reflux, the heating was stopped and the mixture allowed to cool to room temperature. The stirring was stopped after the mixture reached room temperature. After sixty hours, the stirring was restarted and 100 mL of deionized water was added in several small portions over an hour to quench any remaining Grignard reagent. The solution was filtered using #40 Whatman filter paper in a Buechner funnel under water-aspirator vacuum. The tetrahydrofuran was removed from the filtrate using a rotary-evaporator, resulting in a yellow solid (1139.35 g) due to the slight solubility of the magnesium salts in tetrahydrfuran. This solid was dissolved in a mixture of hexanes (total of four liters) and water (one liter) and placed in a large separatory funnel. The water was drained and the organic layer washed with three additional one-liter portions of water. The organic layer was placed in a four-liter bottle and 40 g anhydrous magnesium sulfate were added as a drying agent. The bottle was capped and shaken every 15 minutes for one hour, then allowed to stand 16 hours. The hexanes solution was filtered as described above and the solvent removed using rotary-evaporation. The crude product was a pale yellow liquid (443.63 g) produced an infrared spectrum consistent with the desired product. The filter cake of the salts from the Grignard reaction was suspended in additional tetrahydrofuran and filtered as above. This process was repeated twice. These three washes were combined and the tetrahydrofuran removed using rotary evaporation. This resulted in a yellow solid, from which the remaining salts were removed using the process described above for the main portion of the product, resulting in the isolation of an additional 117.42 g of crude product. Infrared spectroscopy showed the two portions of crude product to be identical. The yield of crude product was 89% of theoretical. The product was purified by fractional vacuum distillation using a 30 cm vacuum-jacketed column filled with stainless steel mesh. The main cuts distilled at about 111° C. at about 4000 Pa. The structure of the product was verified using nuclear magnetic resonance spectroscopy. The purity of the two main cuts was found to be greater than 98% by gas chromatography.

Example 4

Synthesis of a Prepolymer Having Moieties Derived from Salicylic Acid

In a nitrogen-atmosphere glovebox, a 250-mL three-neck round-bottomed flask was outfitted with a teflon-coated magnetic stirring bar, addition funnel with septum, and an adapter with a hose connection and a #11 ACE-THRED (Ace Glass Incorporated, Vineland, N.J.). A dried disposable Pasteur pipet was placed in the ACE-THRED connector, and rubber pipet bulbs placed on the end of the disposable Pasteur pipet and on the hose connection of the adapter. To the flask was added 4.44 g of the monomer synthesized in Example 1, 4.20 g of the monomer synthesized in Example 2, and 8.008 g of dimethyldivinylsilane. The addition funnel was charged with 20.608 g of the monomer synthesized in Example 3. The outfitted flask was then moved to a hood, where the hose connection of the ACE-THRED adapter was connected to a source of nitrogen. The nitrogen line was also connected to a bubbler. The Pasteur pipet was connected to a source of oxygen. A slow flow of oxygen was started. A heating mantle was placed under the flask, with a thermocouple between the mantle and the flask. Two drops of platinum-divinyltetramethyldisiloxane catalyst (2-3% platinum in xylenes) were added to the flask by syringe. The flask was heated until the thermocouple indicated a temperature of 68° C. The disilane from Example 3 was added to the flask dropwise, and the temperature at the thermocouple was maintained at 65-70° C. There was evidence of reaction at this point, so an additional two drops of catalyst were added. The reaction exothermed, reaching a temperature of 125° C. The heating mantle was removed at this point. The viscosity increased as the contents of the flask cooled to room temperature, becoming similar to that of honey. The reaction product was analyzed by NMR. The spectra showed that the reaction had not gone all the way to completion, as evidenced by the presence of signals due to residual silane and vinyl groups.

Running the reaction with a greater amount of catalyst likely would have prevented the exotherm. Further moderate heating, especially if more catalyst was added, would have driven the hydrosilylation reaction to completion.

Example 5

Hydrolysis and Condensation of the Prepolymer of Example 4

A small amount of the prepolymer synthesized in Example 4 was placed in an aluminum weighing boat and spread into a thin film. This film was allowed to cure at ambient laboratory conditions. After about an hour, crystals formed on the surface of the film. The next day, the polymer film was firmly adhered to the aluminum surface and exhibited good strength and resilience when probed by forceps. A sample of the crystalline material was removed and analyzed by NMR, which indicated that the crystals were predominately salicylic acid. Thus, we have shown that this prepolymer releases salicylic acid and forms a resilient and adherent film even when exposed to the relatively low moisture level of conditioned air.

Example 6

Synthesis of a salicylic acid-methylsilane adduct (Compound 3)

In a nitrogen atmosphere glove box, 97.8 g salicylic acid, 81.68 g dichloromethylsilane, and 1307 g anhydrous toluene were added to a 3-L 3-neck round-bottomed flask. The flask was outfitted with a stirring shaft with a polytetrafluoroethylene blade and two septa. The flask was transferred to a hood and a needle connected to a nitrogen line was pushed through one septum, while the other was replaced with a condenser connected to a nitrogen line through a hose adapter. The stirring shaft was connected to an air motor and the reaction mixture was stirred. Then 171.7 g anhydrous pyridine was added to the flask. Fifteen minutes after the addition, the reaction mixture was heated to reflux. The heating was stopped after one hour and the solution allowed to stand at room temperature with stirring over night. The next morning, the flask was put in a freezer for 4 hours, and then the reaction mixture was filtered. The crystalline material was rinsed with additional anhydrous toluene. The toluene was removed from the crude product by rotary evaporation. The crude product was distilled under vacuum, the main fraction distilling at 75° C. at 16 kPa.

Example 7

Synthesis of a salicylic acid-silane adduct (Compound 4)

In a nitrogen atmosphere glovebox, 309.4 g salicylic acid is placed in a dry 3-liter 5-neck round-bottomed flask. The flask is outfitted with a stirring shaft with polytetrafluoroethylene blade, Dewar condenser, thermocouple, septum, and sparge tube. The flask is placed in a container in a hood and the condenser is connected to a nitrogen source with bubbler. The stirring shaft is connected to an air motor. One liter of anhydrous toluene and 197.5 g anhydrous pyridine are transferred to the flask. The sparge tube is connected to a lecture bottle containing 227 g of dichlorosilane. The condenser is filled with a mixture of DRY ICE and acetone. The tub is filled with a mixture of water and ice. When the contents of the flask have cooled, the dichlorosilane is slowly bubbled into the flask. After the addition is complete, stirring is continued for an additional two hours. The ice-water bath is then replaced with a heating mantle and the contents of the flask are allowed to come to room temperature. Stirring is then continued for an additional sixteen hours. The contents of the flask are transferred by cannula to a Schlenk filter tube, which is used to filter the reaction mixture into a dry 3-liter single-neck receiving flask. The residue in the flask is stirred with two additional 300 mL portions of anhydrous toluene, both of which are also filtered into the receiving flask. The toluene is distilled from this flask under vacuum. The flask is placed in a nitrogen atmosphere glovebox, where the crude product is transferred to a dry single-neck 500-mL flask outfitted with a magnetic stirbar. The crude product is distilled under vacuum, yielding the desired monomer, the structure of which is shown as Compound 3 above.

Example 8

Synthesis of a salicylic acid-dimethylvinylsilane adduct (Compound 5)

In a nitrogen atmosphere glovebox, 100 g salicylic acid is placed in a dry 5-liter 4-neck round-bottomed flask. The flask is outfitted with a stirring shaft with polytetrafluoroethylene blade, condenser with valved adapter, thermocouple, and septum. The flask is moved to a hood, where the adapter is connected to a nitrogen line and the stirring shaft is connected to an air motor. Two liters of anhydrous toluene and 180 g chlorodimethylvinylsilane are added to the flask. Stirring is initiated and 120 g anhydrous pyridine are transferred to the flask. The reaction mixture is refluxed for one hour, and then allowed to cool to room temperature. The contents of the flask are transferred by cannula to a Schlenk filter tube, which is used to filter the reaction mixture into a dry 3-liter single-neck receiving flask. The residue in the flask is stirred with two additional 500 mL portions of anhydrous toluene, both of which are also filtered into the receiving flask. The toluene is distilled from this flask under vacuum, yielding crude Compound 5.

Example 9

Synthesis of a fenbufen-dimethylsilane adduct (Compound 6)

In a nitrogen atmosphere glovebox, 10 g fenbufen is placed in a dry 250-milliliter 4-neck round-bottomed flask. The flask is outfitted with a stirring shaft with polytetrafluoroethylene blade, condenser with valved adapter, thermocouple, and septum. The flask is moved to a hood, where the adapter is connected to a nitrogen line and the stirring shaft is connected to an air motor. One hundred milliliters of anhydrous toluene and 5 g chlorodimethylsilane are added to the flask. Stirring is initiated and 3.5 g anhydrous pyridine are transferred to the flask. The reaction mixture is refluxed for one hour, and then allowed to cool to room temperature. The contents of the flask are transferred by cannula to a Schlenk filter tube, which is used to filter the reaction mixture into a dry 3-liter single-neck receiving flask. The residue in the flask is stirred with two additional 100 mL portions of anhydrous toluene, both of which are also filtered into the receiving flask. The toluene is distilled from this flask under vacuum, yielding crude Compound 6.

Example 10

Synthesis of a hydrophilic prepolymer that releases salicylic acid

In a nitrogen atmosphere glovebox, 36.96 g of poly(ethylene glycol) divinyl ether ($M_n$ ca. 240 g/mol) and 5 drops of platinum-divinyltetramethyldisiloxane catalyst (2-3% platinum in xylenes) are placed in a 100-mL 3-neck round-bottomed flask outfitted with a magnetic stirring bar. The flask is outfitted with a pressure-equalizing addition funnel containing 5.00 g of Compound 3 (synthesized in Example 6) and 23.05 g of Compound 4 (synthesized in Example 7), a condenser with a valved hose adapter, and thermocouple well. The flask is placed in a heating mantle on a magnetic stirplate, and the adapter connected to a nitrogen line. The flask is heated to 80° C. with stirring, and then the contents of the addition funnel are added dropwise. The addition rate and heating are controlled to maintain the reaction temperature in the range of 80-100° C. The reaction mixture is maintained at 100° C. for 12 hours, then allowed to cool to room temperature.

Example 11

Synthesis of a hydrophilic prepolymer that releases salicylic acid and fenbufen

In a nitrogen atmosphere glovebox, 36.96 g of poly(ethylene glycol) divinyl ether ($M_n$ ca. 240 g/mol) and 5 drops of platinum-divinyltetramethyldisiloxane catalyst (2-3% platinum in xylenes) are placed in a 250-mL 3-neck round-bottomed flask outfitted with a magnetic stirring bar. The flask is outfitted with a pressure-equalizing addition funnel containing 7.2 g of Compound 6 (synthesized in Example 9) and 23.05 g of Compound 4 (synthesized in Example 7), a condenser with a valved hose adapter, and thermocouple well. The flask is placed in a heating mantle on a magnetic stirplate, and the adapter connected to a nitrogen line. The flask is heated to 80° C. with stirring, then the contents of the addition funnel are added dropwise. The addition rate and heating are controlled to maintain the reaction temperature in the range of 80-100° C. The reaction mixture is maintained at 100° C. for 12 hours, then allowed to cool to room temperature.

Example 12

Single-step synthesis of a polymer that releases salicylic acid

In a nitrogen-atmosphere glovebox, 46.13 g salicylic acid is placed in three-liter three-neck round-bottomed flask, followed by one liter of anhydrous toluene. One hundred grams of freshly distilled 1,8-bis(chlorodimethylsilyl)octane is then added to the flask. The flask is then outfitted with a condenser with a valved hose adapter, a glass stirring shaft equipped with a polytetrafluoroethylene blade, and septum. The flask is moved to a hood, where the flask is placed in a heating mantle connected to a rheostat. The adapter is connected to a nitrogen line and the stirring shaft is connected to an air motor. Stirring is initiated, and 26.4 g anhydrous pyridine is added to the flask. After stirring one hour at room temperature, the contents of the flask are heated to reflux for one hour, then allowed to cool to room temperature. The reaction mixture is filtered into another dry flask using a Schlenk filter tube. Two additional 200-milliliter portions of anhydrous toluene are added to the flask and stirred with the residue. These additional portions of toluene are also filtered and combined with the main portion. The solvent is removed under vacuum until about 500 mL of solution remains. This solution is then further purified by passage through a tube equipped with a fritted disc containing 50 grams of anhydrous silica gel, with care to ensure the product is not exposed to moisture. The silica gel is eluted with a further 100 mL of anhydrous toluene, which is combined with the main portion. The toluene is then removed using a rotary evaporator at full oil pump vacuum, yielding the desired product.

Example 13

A Prepolymer Formulation from the Reactive Prepolymer of Example 12

In a nitrogen atmosphere glovebox, 10 g of the reactive prepolymer is placed in a 100 mL polypropylene beaker. Then 200 milligrams of triethoxyethylsilane and 1 g barium sulfate are added. The mixture is stirred thoroughly until homogeneous.

Example 14

Synthesis of a Reactive Prepolymer with Pendant Crosslinking Sites

One hundred grams of a trimethylsilyl-terminated dimethylsiloxane-methylhydrosiloxane copolymer (3-4 weight percent methylhydrosilane) is placed in a two-liter three-neck round-bottomed flask. One liter of anhydrous toluene and 10 drops of platinum-divinyltetramethyldisiloxane catalyst (2-3% platinum in xylenes) are added to the flask. The flask is then outfitted with a condenser with valved hose adapter, mechanical stirrer, and a pressure-equalizing addition funnel containing 10.5 g of Compound 2 (synthesized in Example 2). The flask is then placed in a heating mantle in a hood, where the adapter is connected to a nitrogen line and the stirrer shaft is connected to an air motor. The reaction mixture is brought to reflux with stirring, and then the contents of the addition funnel are added dropwise. A small sample of solution is removed every few hours. The toluene is evaporated from the sample, which is then analyzed by proton nuclear magnetic resonance spectroscopy and infrared spectroscopy for the presence of residual Si—H bonds. When all Si—H has reacted, the reaction mixture is cooled to room temperature and then filtered through a plug of silica gel to remove the platinum hydrosilylation catalyst. The volatiles are removed using a rotary evaporator, leaving the desired polysiloxane with pendant crosslinking sites.

Example 15

Synthesis of a Monomer Suitable for Alkene Metathesis Polymerization

In a nitrogen atmosphere glovebox, 100 g of 1,5-hexadiene is placed in a 500-mL three-neck round-bottomed flask outfitted with a magnetic stirring bar, followed by 10 drops of platinum-divinyltetramethyldisiloxane catalyst (2-3% platinum in xylenes). An additional 100 g of 1,5-hexadiene and 10 g of the product of Compound 4 (synthesized in Example 7) is placed in a pressure-equalizing addition funnel, which is then attached to the flask. A condenser with valved hose adapter is also attached to the flask, and a septum is placed in the third neck of the flask. The flask is placed in a heating mantle on a magnetic stirplate, the adapter is connected to a nitrogen line, and the reaction mixture is brought to gentle reflux. The contents of the addition funnel are then added dropwise to the stirred solution. After the addition is complete, the reaction is refluxed an additional two hours. A small sample of solution is then removed every few hours. The toluene is evaporated from the sample, which is then analyzed by proton nuclear magnetic resonance spectroscopy and infrared spectroscopy for the presence of residual Si—H bonds. When all of the silane has reacted, the reaction mixture is allowed to cool to room temperature and then filtered through a plug of silica gel to remove the hydrosilylation catalyst. The excess 1,5-hexandiene is then removed by rotary evaporation, yielding the desired monomer.

Example 16

Synthesis of a Reactive Prepolymer by Alkene Metathesis Polymerization

In a nitrogen-atmosphere glovebox, 10 g of the monomer prepared in the previous Example is placed in a 50-mL single-neck round-bottomed flask outfitted with a magnetic stirring bar. The flask is put on a heating mantle on a stirplate, with a thermocouple between the heating mantle and the flask. One hundred milligrams of tricyclohexylphosphine[1,3-bis(2,4,6-trimethylphenyl)-4,5-dihydroimidazol-2-ylidene][benzylidene]ruthenium(IV) dichloride metathesis catalyst is then added to the flask. A vacuum line is then connected to the flask through a valved adapter and a 15 cm Vigreux column. The flask is stirred magnetically and opened to the vacuum line. The flask is heated until the thermocouple indicates a temperature of 60° C. between the mantle and the flask. As the initial foaming subsides, the valve to the vacuum line is opened fully. When the pressure in the flask drops below 10 kPa, an oil diffusion pump is opened to the vacuum line, to further decrease the pressure in the flask. The flask is maintained in this condition until no further bubbling is observed and the pressure maintains a constant value. The contents of the flask are then diluted in 100 mL of anhydrous hexane and filtered through 10 cm of silica gel in a column with an inside diameter of 3 cm to remove the catalyst residue. The column is further eluted with 100 mL of anhydrous hexane. The hexane is then removed from the desired polymer under vacuum.

Example 17

Synthesis of a Reactive Prepolymer by Radical Polymerization

In a nitrogen-atmosphere glovebox, 57.27 g of salicylic acid is placed in a one-liter 3-neck round-bottomed flask outfitted with a magnetic stirring bar. Five hundred milliliters of anhydrous toluene is then added to the flask, followed by 100 g of 3-methacryloxypropylmethyldichlorosilane. The flask is then placed on a magnetic stirplate, stirring is initiated, and 33 g of anhydrous pyridine is added. The contents of the flask are stirred for two hours, and then filtered to remove the pyridinium hydrochloride. The solvent is removed under vacuum, and the crude product recrystallized from anhydrous hexane. Ten grams of this monomer is then placed in a 2-liter single-neck round-bottomed flask outfitted with a magnetic stirring bar. Then 100 grams of methyl methacrylate, 1000 mL anhydrous tetrahydrofuran and 50 milligrams of 2,2'-azobisisobutyronitrile are added to the flask. A condenser with a valved hose adapter is connected to the flask, which is then placed in a heating mantle in a hood. The adapter is connected to a nitrogen line and the reaction mixture is heated to reflux for 18 hours. The solvent is removed under vacuum, to yield the desired reactive prepolymer.

Example 18

Synthesis of a dimethylsilane-salicylic acid adduct

In a nitrogen atmosphere glovebox, 200 g salicylic acid and one liter of anhydrous toluene are placed in a 3-liter 4-neck round-bottomed flask. To the flask is then added 186.65 g of dichlorodimethylsilane. The flask is outfitted with a stirring shaft with a polytetrafluoroethylene blade, condenser with valved hose adapter, thermocouple, and septum. The flask is placed in a hood and the adapter is connected to a nitrogen line. The stirring shaft is connected to an air motor. The mixture is stirred, and 120 g anhydrous pyridine is transferred to the flask. After the addition is complete, stirring is continued for an additional two hours, then the reaction mixture is refluxed for two hours. The contents of the flask are transferred by cannula to a Schlenk filter tube, which is used to filter the reaction mixture into a dry 3-liter single-neck receiving flask. The residue in the flask is stirred with two additional 300 mL portions of anhydrous toluene, both of which are also filtered into the receiving flask. The toluene is distilled from this flask under vacuum. The flask is placed in a nitrogen atmosphere glovebox, where the crude product is transferred to a dry single-neck 500-mL flask outfitted with a magnetic stirbar. The crude product is distilled under vacuum, yielding the desired monomer.

Example 19

Synthesis of a vinylsilane monomer containing two molecules of (S)-(+)-4-Isobutyl-α-methylphenylacetic acid (Ibuprofen)

Inside a nitrogen atmosphere glovebox, 6.85 g methyldichlorovinylsilane and 20 g Ibuprofen were added to a four neck 500 mL round-bottomed flask, followed by 200 g anhydrous tetrahydrofuran. The middle neck of the flask was outfitted with a mechanical stirring blade, the other necks outfitted with a septum, gas adapter and a condenser with another gas adapter attached. The flask was transferred to a hood where a nitrogen line was connected to the gas adapter attached to the flask, the gas adapter connected to the condenser was connected to a bubbler, and the mechanical stirring blade was connected to a stirrer motor. Stirring was initiated, resulting in a hazy white solution. Using a syringe, 11.3 g anhydrous triethylamine was added to the flask through the septum. The reaction mixture turned an opaque white and a white precipitate formed. The reaction was slightly exothermic. The contents of the flask were then refluxed for eighteen hours. The reaction was cooled to room temperature, returned to the glovebox, and the precipitated triethylamine hydrochloride was filtered from the reaction mixture directly into a single-neck 500 mL round-bottomed flask. The flask was attached to a rotary evaporator and the tetrahydrofuran was removed. The crude product was a brown liquid obtained in 23.54 g. The proton NMR of the crude product was consistent with the proposed structure (below). An attempt to purify the crude product was not successful. $^1$H NMR (CDCl$_3$): δ 7.0-7.2, 5.6-6.1, 3.6-3.8, 2.4, 1.8, 1.45, 0.9, 0.4.

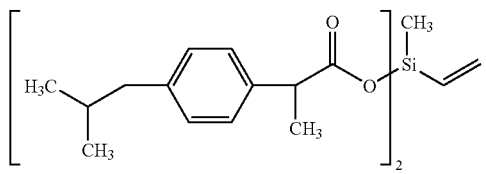

Example 20

Synthesis of a salicylic-releasing polysilane moisture-curing polymer

Into a dry 250 mL round-bottomed flask, 3.26 g (0.0291 mol) dimethyldivinylsilane and 3 drops of the platinum-divinyltetramethyldisiloxane complex catalyst solution were added. The reaction was slowly heated to a temperature of 65° C. and magnetically stirred for ten minutes. Next, 8.83 g (0.0437 mol) 1,6-bis(dimethylsilyl)hexane was slowly dripped into the reaction through a liquid addition funnel. As the first few drops were added, the temperature increased to 85° C. and the colorless liquid turned golden yellow. In addition, the viscosity increased as the color changed. After one hour of stirring at 65° C., the reaction was too viscous to stir magnetically. The temperature of the reaction was increased to 85° C. and magnetic stirring resumed. An NMR was taken to observe the progress of the reaction. No vinyl peaks were present and the integrated signals due to Si—H were as expected. Peaks observed by $^1$H NMR (400 MHz, CDCL$_3$, 25° C.): δ 3.84, 1.35-1.2, 0.98, 0.57, 0.48, 0.34, 0.05, −0.08 ppm.

With the reaction at a steady temperature of 85° C., 6.00 g (0.0291 mol) methylvinyl salicylic acid derivative (Compound 1) was added dropwise. The color of the reaction changed from clear yellow to a milky golden color and the temperature increased slightly. The reaction was stirred for 18 hours. Proton NMR was performed to check the progress of the reaction. All vinyl and hydride peaks were gone, signifying the completion of the reaction. Peaks observed by $^1$H NMR (400 MHz, CDCL$_3$, 25° C.): δ 8.02, 7.51-7.42, 7.10-7.01, 6.88-6.96, 3.65-3.61, 3.56-3.48, 1.26, 0.95, 0.43-0.50, 0.04, −0.04, −0.08 ppm.

Example 21

Synthesis of polyethylene glycol moisture-curing polymer containing salicylic acid-containing monomers In a nitrogen-atmosphere glovebox, four drops of platinum-divinyltetramethyldisiloxane complex catalyst solution and 7.00 g (0.0291 mol) poly(ethylene glycol) divinyl ether were added to an oven-dried 250 mL round-bottomed flask. The reaction was slowly heated to a temperature of 60° C. and magnetically stirred for fifteen minutes. Then 11.77 g (0.0585 mol) 1,6-bis(dimethylsilyl)hexane in a liquid addition funnel attached to the flask was added dropwise. As the first few drops were added, the temperature increased a few degrees and the colorless liquid turned green. The reaction was stirred at 60° C. for approximately three hours and monitored using proton NMR spectroscopy. The disappearance of the signals due to the vinyl protons was used to indicate the progress of the reaction. When they were no longer present, 4.23 g (0.0194 mol) divinyl salicylic acid derivative (Compound 2) was added to the reaction flask. There was no strong exotherm with this addition. After ten minutes, the product became more viscous and changed to a yellow-green color. After an hour of stirring, progress of the reaction was tracked using NMR. Vinyl peaks were still present so the reaction continued overnight at 65° C. The color had changed to a golden tan color the next morning. NMR was again used to check the progress of the reaction. All of the vinyl groups had disappeared and the hydride peak was still present as expected. Finally, 4.00 g (0.0194 mol) of the methylvinylsilyl-salicylic acid derivative (Compound 1) were added to the reaction flask. There was no increase in temperature and the color remained the same. After two hours of reacting, an NMR was taken to check the progress of the reaction. All NMR signals due to the vinyl and Si—H functional groups had disappeared, indicating that the reaction was complete. Peaks observed by $^1$H NMR (400 MHz, CDCL$_3$, 25° C.): δ 8.05-8.0, 7.50-7.42, 7.08-7.01, 6.95-6.90, 3.65-3.61, 3.56-3.48, 1.32-1.2, 1.12-1.09, 0.97-0.92, 0.83-0.77, 0.58-0.40, 0.34, 0.08-0.00, −0.02 to −0.09 ppm.

Example 22

Synthesis of the salicylic-releasing polyethylene glycol moisture-curing polymer and study of its cure at ambient conditions Into a dry 250 mL round-bottomed flask, 2.33 g (0.00971 mol) poly(ethylene glycol) divinyl ether and 3 drops of the platinum-divinyltetramethyldisiloxane complex catalyst were added. The reaction was slowly heated to a temperature of 60° C. and magnetically stirred for ten minutes. Next, 3.92 g (0.0194 mol) 1,6-bis(dimethylsilyl)hexane was slowly dripped into the reaction through a liquid addition funnel. As the first few drops were added, the temperature increased to 72° C. and the colorless liquid turned green. The reaction was stirred at 60° C. for approximately three hours and the progress monitored using proton NMR spectroscopy. The NMR was taken using a 30 second relaxation time and showed that no signals due to vinyl groups remained. Peaks observed by $^1$H NMR (400 MHz, CDCL$_3$, 25° C.): δ 3.81, 3.65-3.61, 3.56-3.48, 1.28, 0.94, 0.56, 0.47, 0.04, −0.04 ppm.

To the reaction flask, 4.0 g (0.0194 mol) methylvinylsilyl-salicylic acid derivative (Compound 1) was added dropwise through a liquid addition funnel. The temperature increased to 70° C. and the color changed from green to a golden yellow after five minutes. The reaction stirred and maintained a temperature of 60° C. for another hour. A proton NMR was taken to check the progress of the reaction. Vinyl peaks and hydride peaks were not present, signifying the polymer was synthesized. Peaks observed by $^1$H NMR (400 MHz, CDCL$_3$, 25° C.): δ 8.15-7.96, 7.5-7.42, 7.08-7.0, 6.94-6.87, 3.64-3.59, 3.54-3.46, 1.25, 1.1, 0.98-0.90, 0.81-0.75, 0.50-0.45, 0.32, 0.05-0.01, −0.05, −0.09 ppm.

The clear yellow polymer changed to a viscous cream-colored product as it cooled.

A gram of the product was placed on an aluminum weighing boat and taken out of the glovebox. The relative humidity present in the air provided water that cured the polymer and released salicylic acid. The sample was placed under a microscope at 4× to observe the white crystals that formed on the surface of the polymer. The crystals were brushed off after 24 hours and a proton NMR was taken. Salicylic acid was the product that bloomed through the polymer as it cured. Peaks observed by $^1$H NMR (400 MHz, CDCL$_3$, 25° C.): δ 7.93, 7.53, 7.01, 6.94 ppm.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. An implantable medical device comprising a coating, the coating comprising a curable material comprising a prepolymer comprising at least one silicon atom and at least one hydrolyzable leaving group bonded to at least one silicon atom, the hydrolyzable leaving group being free of acidic hydrogen atoms, wherein upon hydrolysis of the prepolymer, the prepolymer forms a curable intermediate and the hydrolyzable leaving group is released, and wherein the released hydrolyzable leaving group is a salicylic moiety, wherein the implantable medical device is designed to remain in a subject for more than 28 days.

2. The device of claim 1 wherein the prepolymer comprises a monomer, an oligomer, a polymer, or mixtures thereof.

3. The device of claim 1 wherein the curable intermediate forms a biocompatible polymer upon condensation in the body of a subject.

4. The device of claim 1, wherein the curable intermediate comprises at least two silanol groups.

5. The device of claim 1 wherein the prepolymer is a polymer and further comprises a poly(alkylene oxide) segment, a polysiloxane segment, a polyester segment, a poly(vinyl pyrrolidone) segment, a polyacrylate segment, a polymethacrylate segment, a polycarbonate segment, a hydrocarbon segment, a polycarbosilane segment, a fluoropolymeric segment, a polyoxazoline segment, or mixtures or copolymers thereof.

6. The device of claim 1 wherein the prepolymer comprises one or more silicon atoms per one hydrolyzable group.

7. The device of claim 6 wherein the hydrolyzable group is a terminal group bonded to the silicon atom.

8. The device of claim 1 wherein the prepolymer comprises one silicon atom per one or two hydrolyzable groups.

9. The device of claim 1 wherein the prepolymer comprises one silicon atom per one to three hydrolyzable groups.

10. The device of claim 1 wherein the prepolymer comprises two silicon atoms per one hydrolyzable group.

11. The device of claim 10 wherein the hydrolyzable group is bonded to the two silicon atoms to form a linear polymer.

12. The device of claim 10 wherein the hydrolyzable group is attached to the two silicon atoms to form a ring.

13. The device of claim 1 wherein the prepolymer comprises one or more silicon-bonded hydrolyzable leaving groups pendant from a polymeric chain.

14. The device of claim 1 wherein the curable material further comprises particulate material.

15. The device of claim 1, wherein the curable material is injectable.

16. The device of claim 14, wherein the particulate material is selected from the group consisting of a moisture curing ceramic material, an inorganic material, a polymer microsphere material, a solid polymer particulate material, an imaging particulate material, a woven fiber and a non-woven fiber.

17. An implantable medical device comprising a curable material comprising a prepolymer made from a polymerizable monomer selected from the group consisting of:

a compound of the formula:

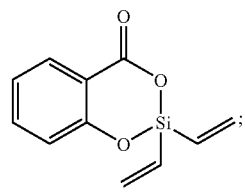

a compound of the formula

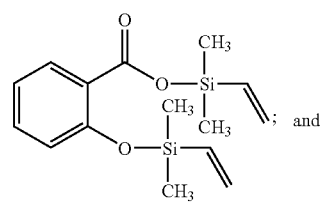

combinations thereof;

wherein upon hydrolysis of the prepolymer, the prepolymer forms a curable intermediate and the hydrolyzable leaving group is released, and wherein the released hydrolyzable leaving group is a salicylic moiety, wherein the implantable medical device is designed to remain in a subject for more than 28 days.

18. An implantable medical device comprising a curable material comprising a prepolymer selected from the group consisting of:

a material of the formula

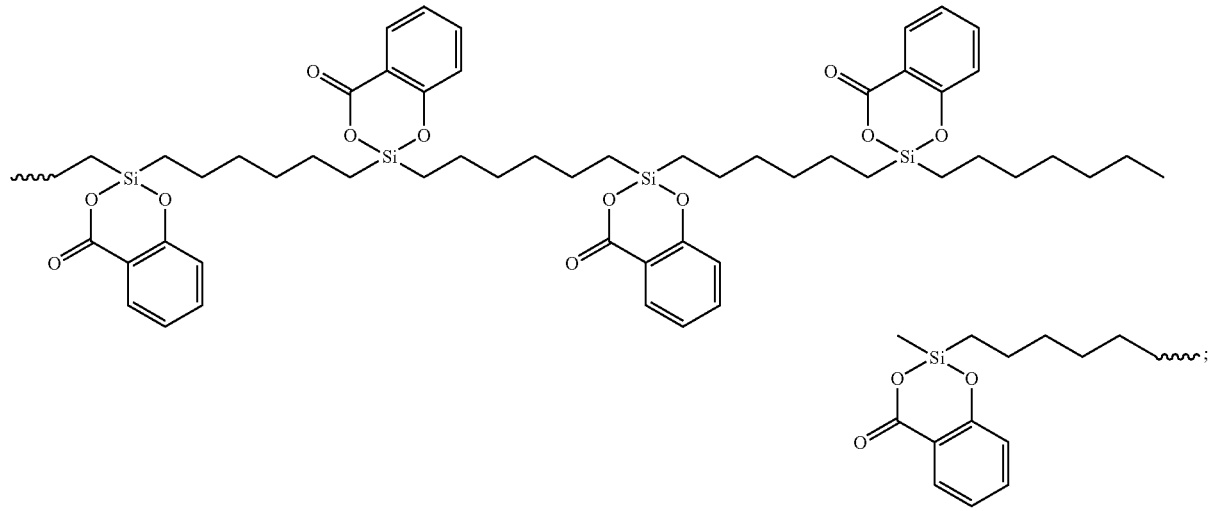

a material of the formula

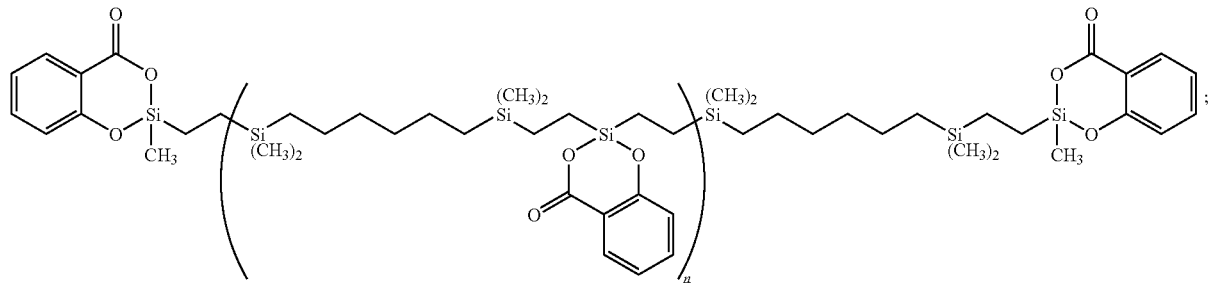

a material of the formula

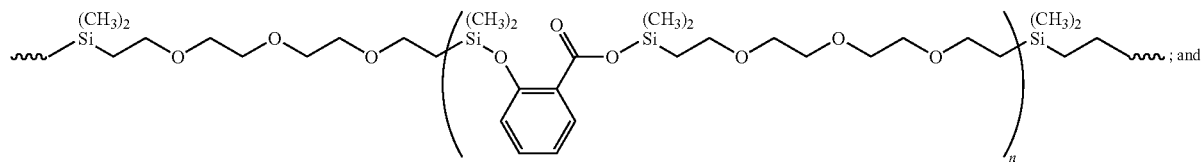

combinations thereof;
wherein upon hydrolysis of the prepolymer, the prepolymer forms a curable intermediate and a hydrolyzable leaving group is released, and wherein the released hydrolyzable leaving group is a salicylic moiety, wherein the implantable medical device is designed to remain in a subject for more than 28 days.

* * * * *